United States Patent [19]

Gawlik et al.

[11] Patent Number: 4,807,837
[45] Date of Patent: Feb. 28, 1989

[54] PORTABLE INTRAVENOUS STAND

[75] Inventors: Gerald M. Gawlik, Wheaton; Robert D. Hoyt, Lombard, both of Ill.; Eugene A. Anderson, 4 N. 463 Babson La., St. Charles, Ill. 60174

[73] Assignee: Eugene A. Anderson, St. Charles, Ill.

[21] Appl. No.: 854,944

[22] Filed: Apr. 23, 1986

[51] Int. Cl.[4] .............................................. A47G 29/00
[52] U.S. Cl. ..................... 248/125; 211/196; 248/188.5; 248/188.6; 248/434
[58] Field of Search ............ 248/125, 188.5, 188.6, 248/188.7, 528, 150, 151, 157, 165, 167, 434, 435, 170, 171, 155.2, 155.3, 311.3; 211/196, 205, 85, 100, 171

[56] References Cited

U.S. PATENT DOCUMENTS

| | | | |
|---|---|---|---|
| 542,609 | 7/1895 | Gordon et al. | 248/155.3 |
| 742,582 | 4/1903 | Jones | 211/172 |
| 768,363 | 8/1904 | Harrell | 211/172 |
| 906,963 | 12/1908 | Thompson | 248/170 X |
| 1,185,642 | 6/1916 | Emerson | 248/435 X |
| 1,832,730 | 11/1931 | Pack | 211/171 |
| 2,445,489 | 7/1948 | Mangold | 248/171 X |
| 2,542,137 | 2/1951 | Hanson | 248/171 |
| 2,673,771 | 3/1954 | Krewson | 248/311.3 X |
| 3,064,932 | 11/1962 | Holderman | 248/188.5 X |
| 3,287,040 | 11/1966 | Verticchio | 248/188.5 X |
| 3,464,664 | 9/1969 | Nugent | 211/172 X |
| 3,804,355 | 4/1974 | Uroshevich | 248/170 X |
| 3,941,250 | 3/1976 | Ott | 211/100 X |
| 4,332,378 | 6/1982 | Pryor | 248/125 X |
| 4,541,596 | 9/1985 | Price | 248/159 X |

Primary Examiner—Ramon O. Ramirez
Attorney, Agent, or Firm—Michael J. Femal

[57] ABSTRACT

A portable, light weight, collapsible IV stand includes telescoping height adjustable hollow tubing sections having IV bag support arms pivoted from a storage position within the top tubing section to a use position locked in a horizontal plane. The IV stand further includes support legs that are stored within the bottom section of tubing and they are extended into a stable tripod configuration in their use position.

4 Claims, 3 Drawing Sheets

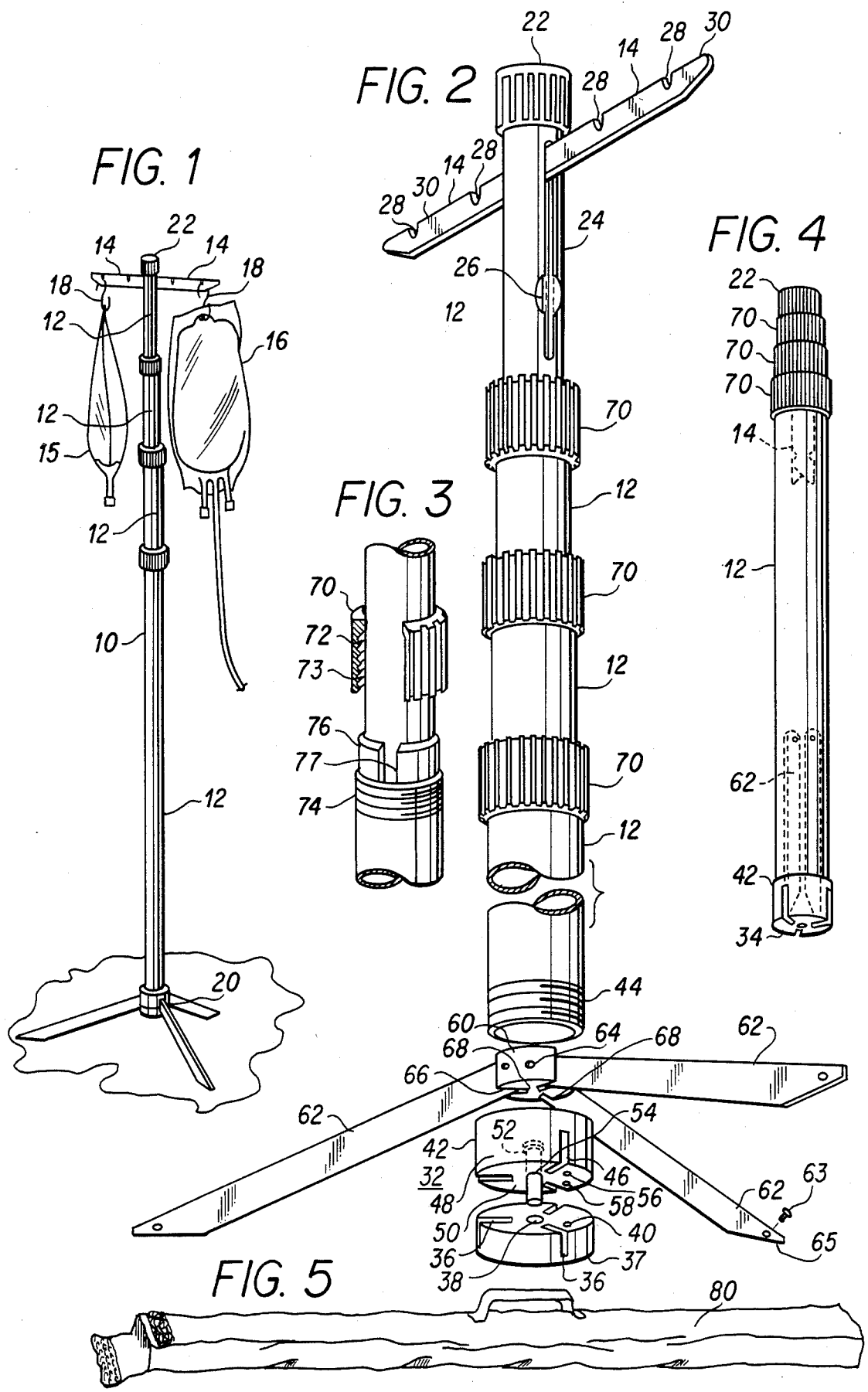

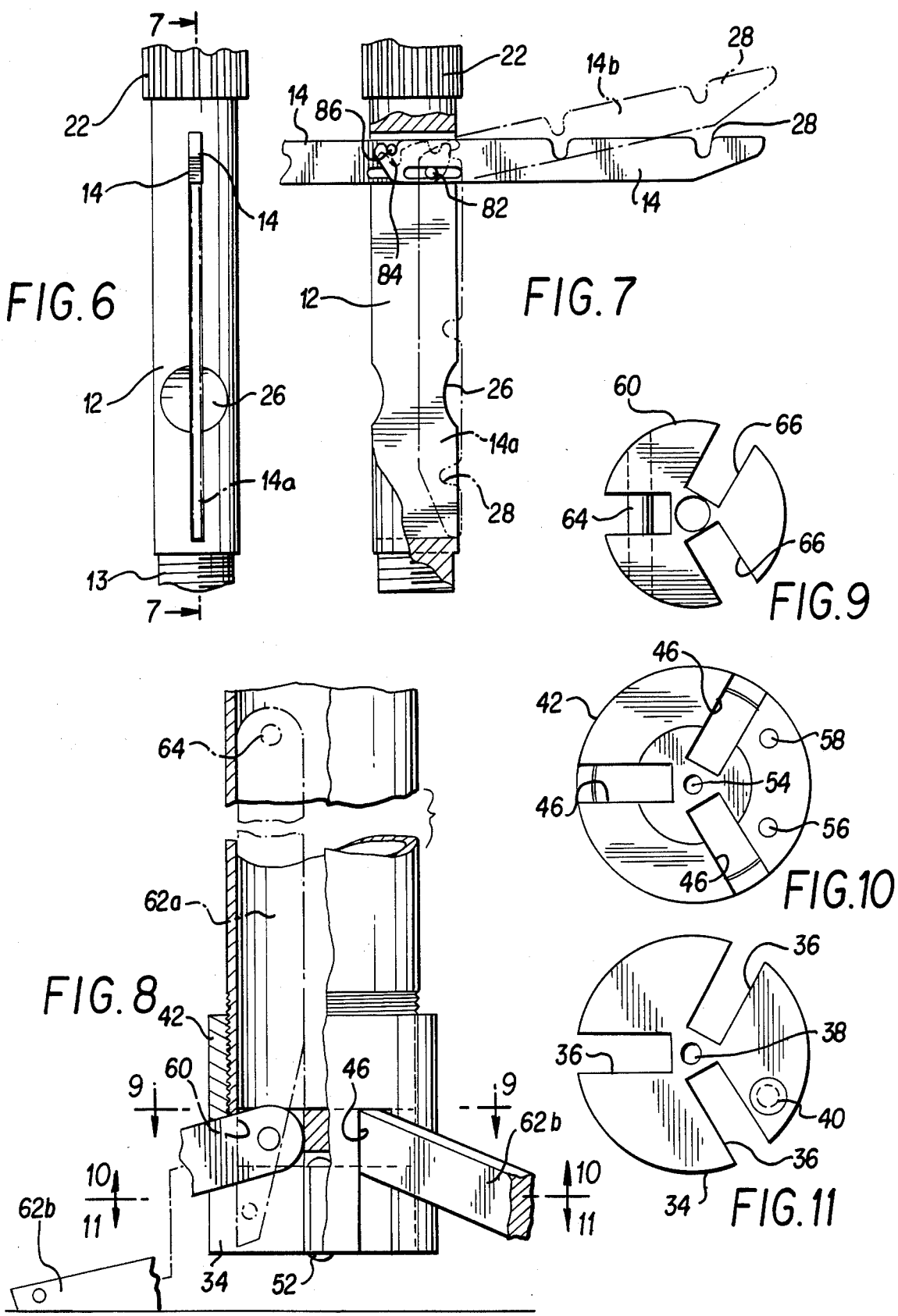

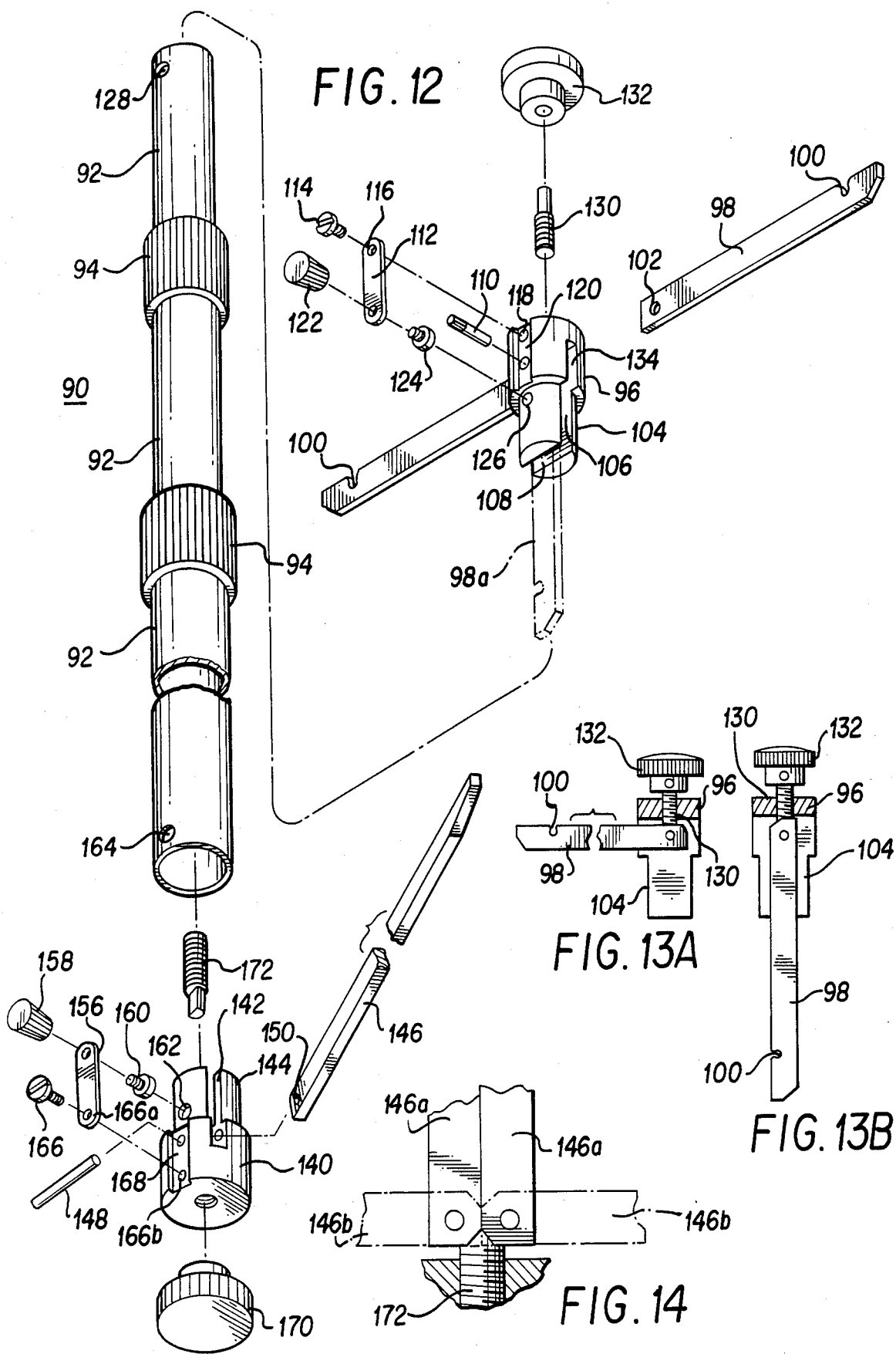

PORTABLE INTRAVENOUS STAND

BACKGROUND OF THE INVENTION

With the rising medical costs, the current emphasis in medical care is to send the patient home sooner to convalesce. Many recuperating patients still require the administration of various types of intravenous fluids. Ordinary beds in the homes are seldom equipped with intravenous poles as shown in U.S. Pat. No. 4,113,222. Moreover, the typical hospital designed intravenous stands which are separate from the beds and might be used in the home setting are too heavy and cumbersome to be practical for home use. In addition, these hospital IV stands seldom are adjustable in height along with being too heavy for the patient, nurse or family members to easily maneuver the stand about in the home environment.

In short, there is a need for a light weight, portable and adjustable IV stand which can be used in the home environment without causing severe problems for the user.

SUMMARY OF THE INVENTION

This invention relates to a portable IV stand, and, more particularly, to a portable IV stand which can be conveniently used and set up by any family member or even brought by a doctor or nurse during a home call.

It is an object of the invention to provide a portable IV stand that includes all of the important features of a conventional IV pole or stand yet is easy to set up, sturdy and compact.

It is still another object of the invention to provide a portable IV stand that can fold up into a convenient size so that it may be carried into the home environment and then set up by most family members without assistance.

It is a further object of this invention to provide a portable IV stand that is light in weight, maneuverable and adaptable to use in the home environment.

It is yet a further object of this invention to provide a portable IV stand that utilizes improved materials while reducing overall costs associated with medical devices.

Still further advantages of the present invention will become apparent from the following detailed description wherein reference is made to the drawings.

BRIEF DESCRIPTION OF THE DRAWINGS

FIG. 1 is a perspective view of the invention;

FIG. 2 is an exploded perspective view of FIG. 1;

FIG. 3 is a fragmentary view showing the means of fixing the telescoping tubular sections with respect to one another;

FIG. 4 is a side-elevation view of the invention in the collapsed and unused position;

FIG. 5 is the carrying case for the invention when in its state as shown in FIG. 4;

FIG. 6 is a side-elevation view of the upper IV carrier portion of the stand;

FIG. 7 is a view taken along line 7—7 in FIG. 6;

FIG. 8 is a fragmentary elevation view of the lower support members of the invention in FIG. 1;

FIG. 9 is a view taken along line 9—9 of FIG. 8;

FIG. 10 is a view taken along line 10—10 of FIG. 8;

FIG. 11 is a view taken along line 11—11 of FIG. 8;

FIG. 12 is an exploded perspective view with parts broken away of an portable IV stand according to another embodiment of the invention;

FIG. 13a and 13b are cross sectional views showing the IV arm support means with the arms in the extended for use and stored positions, respectively, of the invention of FIG. 12; and FIG. 14 is a cross sectional view of the leg supports means for the invention of FIG. 12.

DETAILED DESCRIPTION OF THE INVENTION

Referring to FIG. 1, a light weight, collapsible and portable IV stand 10 preferably made from a plurality of telescopically interconnected tubular sections 12 is shown. A pair of pivotally mounted IV support arms 14 extend outwardly and perpendicularly from the uppermost tubular section 12 for supporting at least one or more IV bags 16 from a hook 18 or the like. The IV stand 10 includes a leg support means 20 to be described in greater detail later. The components and tubular sections 12 are preferably made out of aluminum or other light alloy metal.

Turning now to FIG. 2, the upper tubular section 12 includes a cap 22 on its top. This section 12 also includes a longitudinal slot 24 therethrough having a pair of indent digits 26 on opposite sides of the tubular section 12 bisected by the slot 24. The arms 14 are pivotally mounted within the slot 24 and are shown in their operative position, i.e., rotated upwardly and locked in place as will be described in greater detail later. The arms 14 generally have one or more notches 28 on their top surface 30 when in the operative position. In the stored position the arms 14 pivot into the slot 24 from opposite sides on the tube section 12 and the indent digits 26 permit the user to grasp the arms 14 and pivot them upward from their stored location within the tube 12. The uppermost tubular section 12 comprises a circumference slightly smaller than the next lower tube section 12. The IV stand 10 comprises two or more hollow telescoping tubular sections and each lower tubular section 12 has a larger circumference than the one above so that the one above can telescope into the lower one to form a collapsible, portable IV stand.

The lowest tubular section 12 is attached to a multipiece lower leg support bracket 32. The bracket 32 comprises a lower locking disc 34 having three slots 36 spaced equidistant on its circumference and extending inwardly toward a hole 38 in the center of the disc 34. A ball detent 40 is located on the topside of the disc 34. A guide disc 42 forms a cap over the end of the lowermost tubular section 12 with inner threads to fixedly attach it to the lower end threads 44 on tubular section 12. The guide disc 42 includes three L-shaped slots 46 spaced equidistant on the circumference of the guide disc 42 extending down its longitudinal length 48 and across its bottom surface 50. The portion of the slots 46 extending across its bottom surface 50 coincide with the physical size of the slots 36 generally, on the locking disc 34. A pin 52 affixes the locking disc 34 to the guide disc 42 in a rotating relationship. The pin 52 extends through a hole 54 in the center of guide disc 42 and the hole 38 in the locking disc to rotatingly affix them together. A first detent 56 on the bottom surface 50 of guide disc 42 aligns the slots 36 with slots 46. A second detent 58 misaligns the slots 36 and 46 in a locking configuration when the ball detent 40 engages the second detent 58 on the discs 34 and 42, respectively. The detents 56 and 58 are engaged by the ball detent 40 when the locking disc 34 is rotated with respect to the fixed guide disc 42.

Next, a tripod support disc 60 is slideably received within the lower tubular section 12. The tripod disc 60 acts as a carrier and support for triplicate legs 62 which are pivotally mounted within the disc 60 by pins 64 located at one end of each leg 62. Each leg 62 rotates about the axis of each pin 64 fixedly attached to disc 60. The disc 60 further includes triplicate slots 66 spaced equidistant from each other on the circumference of the disc 60. The slots 66 align with the slots 36 and 46 on discs 34 and 42, respectively. A pin 63 is located at a tip 65 of each leg 62. The pins 63 are of a sufficient length to prevent the tips 65 of each leg 62 from passing completely through the slots 46 of disc 42. This interference engagement of pins 63 with slots 46 prevent the legs 62 and carrier disc 60 from dropping back into the lowermost tubular section 12.

Now the disc 60 slides up within the lower most tubular section 12 to the predetermined interference engagement as previously stated and the legs 62 rotate to a generally perpendicular position with respect to a bottom surface 68 on the disc 60 when the legs 62 are drawn up within the tubular section 12 for storage. Further, in the storage position, the legs 62 are locked up within the tubular section 12 and engaging the slots 46 at their pins 63 by rotating the disc 34 so that the ball detent 40 on disc 34 engages detent 58 on guide dics 42. In this position of storage, the legs 62 are principally drawn up within the tubular section 12 having the pins 63 fitted into recesses integral with the slots 46 but the pins 63 do not pass all the way through the slots 46 or disc 42.

FIG. 3 shows a cross section of a knurled nut 70 having a central hole therethrough sufficient to pass the diameter of the next tubular section 12 extending thereabove. Under the upper surface of the nut 70 is a beveled surface 72 that extends downward to inner threads 73 thereof. A threaded top 74 of each tubular section 12 telescopically engages the tubular section 12 thereabove. A split beveled ring 76 engages the top threaded portion 74 of the lower tubular section 12 at one end and surrounds the circumference of the upper tubular section 12 telescoping into the lower tubular section 12. The ring 76 includes a slit 77 that extends its length. Thus, when the nut 70 is tightened on the threads 74 on the lower tubular section 12, the split ring 76 binds against the surface of the upper tubular section 12 therewithin and frictionally fixes the upper and lower tubular sections with respect to one another. Therefore, an operator loosens and tightens the nuts 70 on the stand 10 to adjust the appropriate overall length of the IV stand 10. In addition, the top threaded portion 74 of each lower tubular section 12 may be slit and have an upper beveled edge integral therewith to replace the split ring which would perform the same function as the split ring 76 in operation.

Referring now to FIG. 4, the IV stand 10 is in its collapsed state in which the arms 14 and legs 62 are in their stored position within the sections 12. To place the IV stand 10 in an operative mode, disc 34 is rotated so that its slots 36 align with slots 46 on guide disc 42 or in other words, the disc 34 is rotated so its ball detent 40 engages detent 56 on the guide disc 42. A simple shake or simply gravity causes the legs 62 to slide through slots 46 and 36 until tripod disc 60 rests on the inner bottom surface of guide disc 42. Then the legs 62 rotated upwardly until they engage the top of the vertical portion of the slots 46 whereupon the disc 34 is rotated until the ball detent 40 engages the detent 58 on guide disc 42 locking the legs in a stable tripod configuration to support the IV stand in the upright position as shown in FIG. 1.

FIG. 5 shows a suitable carrying case 80 for transporting the portable IV stand to a final destination for use. The case of course can be made of any fabricate like nylon or the like.

FIG. 6 shows the arms 14 in their extended for use position and more particularly, the construction of the uppermost tubular section 12 with the support arms 14. Although this portion of the tubular section 12 supporting the arms 14 could be hollow like the remaining sections 12, it instead is made up of a two-piece construction. What is shown in FIG. 6 is one half of the upper most tubular section 12. This piece is of a solid construction such as a suitable plastic which a thread 13 is cut into its lower end. This thread 13 mates with the inner threads cut into the top of the other half of the upper most tubular section 12. When both halves are connected, they form one tubular section 12 which telescopes in the next lower tubular section 12 as described before herein. The indent 26 permits the insertion of a thumb and index finger to grip and pull the arm 14 out of its stored position within the solid upper half of the upper most tubular section 12.

FIG. 7 shows how an arm 14 is pulled from its stored position and placed into its operative position. The arm 14 is shown in a stored position as 14a. Fingers are inserted at indent 26 and the arm 14 is raised to a height 14b and then slid back along guide pin 82 until a rear notch 84 on each arm 14 is hooked underneath locking pin 86. Then the arm 14 is lowered into its operative horizontal position.

Referring now to FIG. 8, the operation of setting up the tripod legs 62 is shown in still greater detail. When the legs 62 are in their stored position 62a, the tripod disc 60 is located in its stored position 60a. If the locking disc 34 is rotated aligning its slots with those slots on guide disc 42, the legs drop down into their fully extended position with tripod disc 60b engaging the bottom inner surface of guide disc 42. Then the legs 62 are rotated upwardly into their support position and disc 34 is rotated locking the legs 62 in position 62b with the ball detent 40 engaging detent 58.

FIG. 9 shows the disc 60 and leg pin 64. FIG. 10 shows the guide disc 42 having slots 46 and extending and locking detents 56 and 58, respectively. FIG. 11 shows locking disc 34 including slots 36 and ball detent 40.

Turning now to FIG. 12, an alternative embodiment of the present invention is shown. A portable IV stand 90 includes telescoping tubular sections 92 like tubular sections 12 which are adjusted with respect to one another by locking nuts 94 functioning identical to locking nuts 70. The principle difference is in the structure of the support means for the arms and legs of the IV stand.

A top bracket 96 for supporting a pair of IV arms 98 having one or more notches 100 and pivot pin hole 102 fits into the top of the uppermost 92 by a circular shank 104. The top bracket 96 includes a slot 106 extending from an opening 108 in the bottom of the shank 104 to almost the top surface of the bracket in which the arms 98 are rotated from a storage position to an extended for use position. The arms 98 are held in place by an arm pivot pin 110. In the stored position 98a the arms 98 extend in line with the axis of the shank and fit within tube 92 when the shank 104 is inserted into the top of the tube 92. The top bracket 96 is held in place with its shank 104 within the tube 92 by a flat spring 112 attached by a retention screw 114 inserted through a hole 116 in the spring 112 and then into a screw hole 118 within a keyed slot 120. A knob detent formed by a knob 122 and screw 124 retains the top bracket 96 in a removable fixed relationship to the tube 92 by the screw 124 extending through a hole 128 on the top of the tube 92 and aligns with a hole 126 on the shank 104 on the top bracket 96. To remove the top bracket 96, the operator pulls the knob 122 away from the tube 92 releasing the detent screw from holes 126 and 128 allowing the top bracket 96 to be removed from the tube 92. Once removed, the arms 98 can be changed from the storage position to the operative position. The arms 98 are held in the storage position by a upper lock screw 130 turned by a knob 132. Unscrewing the lock screw 130 permits the arms 98 to be rotated freely about pivot pin 110. The arms are pivoted from the storage position 98a to an operative position generally horizontal to the floor and perpendicular to the tubes 92.

The arms 98 are slid sidewise on the pivot pin 110 to rectangular slots 134 on opposite sides of the slot 106. Next the screw 130 is tightened and passes between the two arms 98 locking them in place in the rectangular slots 134. Then the shank 104 of the top bracket 96 is reinserted into the tube 92 having the detent screw passing through hole 128 and engaging 126 to lock the bracket 96 securely within the top tube 92 of the IV stand.

Similarly, a bottom bracket 140 is constructed with striking similarities to the top bracket 96. The major difference is that the bottom bracket includes three slots 142 spaced equidistant around the circumference of a shank 144 for insertion into the bottom tube 92 of the stand. Triplicate support legs 146 are pivotally mounted within the bracket 140 by pins 148 passing through a pivot hole 150 at one end of each leg 146. The legs 146 are rotated about the pivot pins 148 so they extend along the axis of the shank 144 and can be inserted within the tube 92 for storage. A spring 156 includes a locking knob and screw 158 and 160, respectively, that permits the screw 160 to pass through a hole 164 on the tube 92 into a locking hole 162 on the shank 144 when the shank is inserted within tube 92. The spring 156 is held in place by a screw 166 passing through a hole 166a on the spring into a screw hole 166b in a keyed slot 168 on the top portion of the bracket 140. A locking knob and screw, 170 and 172, respectively, operates identical to the screw 130 and knob 132 on the top bracket 96 to lock the legs in the storage and operative positions.

FIG. 13a shows one of the arms 98 in the extended operative position with the locking knob and screw locking the arms in place for use by passing the screw 130 between the two arms 98 and locking them in their horizontal slots 134 in the bracket 96. FIG. 13b shows the arms 98 in the storage position with the screw 130 bearing down on the rear end of the arm within the bracket to lock it in the storage position.

FIG. 14 shows the legs 146 extended in the storage position 146a and then swung down to engage the locking screw 172 in a tripod adjusting position 146b. As the operator turns the knob 170, the screw 172 pushes upwardly causing the legs 146 in their 146b position to move downwardly forming the tripod leg support. The screw 172 bearing against the end of each leg 146 locks them in tripod support position. Thus, the screw 172 locks them in both the storage and use positions by rotating the knob 170. When the legs 146 are lowered from the horizontal position 146b to the use position then a very stable tripod stand is formed by those legs 146.

Although two embodiments of the invention have been illustrated in the accompanying drawings and described in the foregoing detailed description, it will be understood that the invention is not limited to just the embodiments disclosed, but is capable of numerous rearrangements, modifications and substitution of components without departing from the scope of the invention.

We claim:

1. An intravenous stand for dispensing intravenous fluids, comprising:
   a plurality of elongated tubes partially disposed within each other in a telescoping relation with respect to one another;
   means for adjusting the telescoping tubes to fix the overall height of the stand;
   means integral with the uppermost tube of the stand for supporting an intravenous bag having a pair of oppositely extending support arms pivotally mounted therein to rotate from a storage position entirely within the tube to a use position generally perpendicular to the tube axis and notched for IV bags; and
   means integral with the lowermost tube of the stand for supporting the stand in an upright position having at least three legs pivotally mounted therein to rotate from a storage position within the tube to a tripod support configuration for using the stand, wherein the tubes telescope generally into the lowermost tube to form a collapsible, compact and portable stand generally the length of the lowermost tube for easy transport of the stand and wherein the intravenous support means comprises a solid upper half of the uppermost tube having a slot extending longitudinally and bisecting its center for storing the arms and having generally circular indents on opposing sides thereof bisected by the slot for inserting a digit to grasp the arm and rotate it upwardly into its fixed support position for use.

2. The stand of claim 1 wherein the intravenous support means comprises a removable top bracket having the support arms pivotally mounted therein to rotate from a storage to use position when the bracket is first removed and then the bracket is reinserted into the uppermost tube and fixedly locked in place.

3. The stand of claim 1 wherein the tripod support means includes a locking disc with slots, a guide disc with slots and a tripod support disc having the legs pivotally mounted thereto wherein the locking disc is rotated with respect to the guide disc allowing the legs to extend from their storage position within the lowermost tube to their stand support position and then the locking disc is rotated to lock the legs in place for use.

4. The stand of claim 1 wherein the tripod support means comprises a bottom bracket having the three legs pivotally mounted therein with slots spaced equidistant around its circumference, the bottom bracket is removably received within the lowermost tube and when the bracket is removed the legs are rotated from their storage to use position and locked in place before the bracket is reinserted into the tube for providing the tripod support configuration for the stand in use.

* * * * *